US00PP21471P2

(12) United States Plant Patent
Kordes

(10) Patent No.: US PP21,471 P2
(45) Date of Patent: Nov. 16, 2010

(54) HYBRID TEA ROSE PLANT NAMED 'KORPENPARO'

(50) Latin Name: *Rosa hybrida*
Varietal Denomination: KORpenparo

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/583,070

(22) Filed: Aug. 12, 2009

(51) Int. Cl.
*A01H 5/00* (2006.01)

(52) U.S. Cl. ..... Plt./133
(58) Field of Classification Search ..... Plt./133
See application file for complete search history.

(56) References Cited

OTHER PUBLICATIONS

2008/1243, European Union CVPO summary, Aug. 15, 2008, European Union.

*Primary Examiner*—Susan B McCormick Ewoldt

(57) ABSTRACT

A new and distinct variety of rose with long lasting, novel cream white flowers, and attractive foliage with good disease resistance. It exhibits uniform, upright to bushy growth with abundant flowers. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross-referenced or related applications. This variety was developed without the aid of any research grant.

Genus, species and variety denomination: The botanical classification of the new rose plant is *Rosa hybrida,* 'KORpenparo'.

BACKGROUND OF THE INVENTION

The new variety of rose plant of the present invention originated from a controlled crossing made in a rose breeding program between 'MEIcapinal' and 'NOAsia'.

The controlled crossing was made during the summer of 2000. The following winter, Tim-Hermann Kordes planted the resulting seeds from the aforementioned hybridization in a glasshouse where they subsequently germinated and grew. Evaluations and observations were made on the resulting seedlings in a controlled environment in Offenseth-Sparrieshoop, Germany. The resulting seedlings exhibited distinctive physical and biological characteristics. The new rose plant 'KORpenparo' was selected in May, 2000 from the seedling beds to be asexually propagated for further evaluation. The first asexual reproduction of 'KORpenparo' was done by rooting softwood cuttings in July, 2001 at the Rosa-Danica Nursery in Odense, Denmark.

This initial and other subsequent propagations conducted in controlled environments show that the foregoing and all other characteristics of 'KORpenparo' come true to form and are transmitted through succeeding generations.

SUMMARY OF THE INVENTION

The new rose plant may be distinguished from its seed parent, 'MEIcapinal' by the following combination of characteristics:

1. The flower color of 'MEIcapinal' is pink, while the flower color of 'KORpenparo' is cream white.
2. The petal count of 'MEIcapinal' is double, while the petal count of 'KORpenparo' is very double.

The new rose plant may be distinguished from its pollen parent, 'NOAsia' by the following combination of characteristics:

1. The flower color of 'NOAsia' is pink, while the flower color of 'KORpenparo' is cream white.
2. The petal count of 'NOAsia' is semi-double, while the petal count of 'KORpenparo' is very double.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpenparo' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpenparo' was selected in May, 2000 from the seedling beds to be asexually propagated for further evaluation. The first asexual propagation of 'KORpenparo' was done by budding to seedling understocks in August, 2001 at the inventor's nursery in Offenseth-Sparrieshoop, Germany.

This initial and other subsequent propagations conducted in controlled environments demonstrate that 'KORpenparo' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORpenparo'.

DETAILED BOTANICAL DESCRIPTION

The following is a description of 'KORpenparo', as observed growing in October, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORpriggos', a rose variety from the same inventor described and illustrated in U.S. Plant patent application Ser. No. 11/893,516 and filed on Aug. 15, 2007 are compared to 'KORpenparo' in Chart 1.

CHART 1

| Characteristic | 'KORpenparo' | 'KORpriggos' |
|---|---|---|
| Flower color, ¼ open | Upper surface: Yellow Group 2D. Lower surface is Yellow Group 2D. | Upper surface: Orange-White Group 159D. Lower surface, marginal zone: White Group 155D. Transitions to a large marginal zone of Yellow Group 2D. |
| Petal count | Flower is double to very double, with approximately 45 petals. | Flower is double to very double, with 45-50 petals on average. |

Parents:

*Seed parent.*—'MElcapinal'.

*Pollen parent.*—'NOAsia'.

Classification:

*Botanical classification.*—*Rosa hybrida,* 'KORpenparo'.

*Commercial classification.*—Hybrid Tea.

FLOWER AND FLOWER BUD

Blooming habit: Recurrent.

Flower bud:

*Size.*—Upon opening, 30-35 mm in length from base of receptacle to end of bud and 30-35 mm diameter at its widest point.

*Bud form.*—Short and globular.

*Bud color.*—As sepals first unfold, bud color is Yellow Group 2D. When ¼ open, the upper surface of petals is Yellow Group 2D and the lower surface is Yellow Group 2D.

*Sepals.*—Size: Average 24-26 mm long×11-14 mm wide. Shape: Sepals generally subulate. Sepal apex is generally cirrose. Weak foliaceous appendages on three of the five sepals. Base is flat at union with receptacle. Quantity: Five. Margins: With stipitate glands on sepals with appendages. Surface texture: Inner side: Covered in fine white hairs. Outer surface: Smooth. Stipitate glands are absent. Color: Upper surface Green Group 138A. Lower surface Yellow-Green Group 144A.

Receptacle:

*Surface.*—Smooth.

*Color.*—Yellow-Green Group 144A.

*Shape.*—Funnel shaped.

*Size.*—8 mm (h)×10 mm (w).

Peduncle:

*Surface.*—With stipitate glands.

*Length.*—40-50 mm average length.

*Diameter.*—4-5 mm average diameter.

*Color.*—Yellow-Green Group 144B.

*Strength.*—Moderate.

*Borne.*—Multiple buds. 3-5 buds per flowering stem.

*Anthocyanin.*—Present. Greyed-Purple Group 184B.

Flower bloom:

*Fragrance.*—Light to moderate.

*Duration.*—On the plant 8 to 10 days. Long lasting. As a cut flower, 6 to 8 days. Senesced petals drop away cleanly.

*Size.*—Large flowered garden rose. When open, the average flower diameter is 90-110 mm and the average flower height is 55 mm.

*Form.*—Shape of flower when viewed from the side: Upon opening, upper part: Flattened convex. Upon opening, lower part: Concave. Open flower, upper part: Flattened convex. Open flower, lower part: Concave.

Color:

*Upon opening, petals.*—Outermost petals: Outer Side: Yellow Group 4D. Inner Side: Yellow Group 4D. Innermost petals: Outer Side: Yellow Group 9D. Inner side: Yellow Group 9D.

*Upon opening, basal petal spots.*—Basal petal spot, outermost petals: Outer Side: Yellow Group 2B. Inner Side: Yellow Group 2B. Basal petal spot, innermost petals: Outer Side: Yellow Group 2A. Inner Side: Yellow Group 2A.

*After opening, petals.*—Outermost petals: Outer Side: White Group 155B. Inner Side: White Group 155B. Innermost petals: Outer Side: Yellow-White Group 158B. Inner Side: Yellow-White Group 158B.

*After opening, basal petal spots.*—Basal petal spot, outermost petals: Outer Side: Yellow Group 2B. Inner Side: Yellow Group 2A. Basal petal spot, innermost petals: Outer Side: Yellow Group 2A. Inner Side: Yellow Group 2A. Variegations: None.

General tonality: On open flower Yellow-White Group 158B. No change in the general tonality at the end of the $4^{th}$ day. Afterwards, general tonality is White Group 155C.

Petals:

*Petal count.*—Approximately 45 petals under normal conditions.

*Petal reflex.*—Petals reflex slightly.

*Petal edge.*—Ruffled.

*Petal shape.*—Deltoid. Apex shape is round. Shape of base is deltoid.

*Petal size.*—40 mm long; 40 mm wide.

*Thickness.*—Thick.

*Petal arrangement.*—Generally in a regular pattern with overlapping edges.

Petaloids: Present.

*Petaloid count.*—Average of 8-10 per flower.

*Petaloid edge.*—Ruffled.

*Petaloid texture.*—Wrinkled.

*Petaloid shape.*—Linear to elliptic.

*Petaloid size.*—Petaloids are 15-18 mm long and 8-15 mm wide.

*Petaloid color.*—Color of inner side is Yellow Group 10C. Color of outer side is Yellow-Orange Group 14D.

Reproductive organs:

*Pistils.*—Approximately 25 present. Stigmas: Location: Slightly inferior in position to anthers. Color: Green-Yellow Group 1C. Styles: Length: 5-6 mm long. Color: Yellow-Green Group 154D. Intonations of Red Group 52B.

*Stamens.*—Approximately 75 on average and regularly arranged. Anthers: Size: 3.5-4.0 mm long. Color: Yellow-Orange Group 20A and Yellow-Orange Group 20B. Pollen: Absent. Filaments: Color: Red-Purple Group 58B. Length: 7 mm.

THE PLANT

*Plant growth.*—Vigorous. Upright to bushy habit. When grown as a budded nursery plant the average plant height is 75-80 cm and the average plant width is 45-50 cm.

*Stems.*—Stem color: Young wood: Yellow-Green Group 146B. Older wood: Yellow-Green Group 146B. Stem surface: Young wood: Smooth. Older wood: Rough.

*Prickles.*—Present. Incidence: 15-18 per 10 cm of stem. Size: Average length: 10-11 mm. Color: Immature prickles: Red-Purple Group 60B. Mature prickles: Greyed-Red Group 178B. Senescing to Greyed-Orange Group 174C. Shape: Concave. Anthocyanin: Color: Greyed-Purple Group 185B.

*Leaves and leaflets.*—Normally 3-5 leaflets on normal leaves in middle of the stem. Leaf size: 60 mm (1)× 110 mm (w). Quantity: Moderate. Texture: Upper side of leaflet: Semi-glossy. Leathery. Under side of leaflet: Matte. Rough. Leathery. Color, mature foliage: Upper Leaf Surface: Green Group 137A. Lower Leaf Surface: Yellow-Green Group 146B. Color, juvenile foliage: Upper Leaf Surface: Yellow-Green Group 146A. Lower Leaf Surface: Yellow-Green Group 146B. Anthocyanin intonation: Present. Location: Intonations present on juvenile leaf margins, developing leaves, peduncles, petiole, and stems. Color: Greyed-Purple Group 184B.

*Stipules.*—Size: 25-30 mm long. 9-10 mm between the tips of the stipule. Main body of stipule 10-13 mm in width. Shape: Longitudinally flanged or winged along middle. Stipule color: Green Group 138A. Anthocyanin: Greyed-Purple Group 184B. Presence of stipitate glands: Present on margins. Margins: Serrated. With stipitate glands.

*Petiole.*—Length: 20 mm. Diameter: 2.5 mm. Petiole color: Green Group 138A. Anthocyanin present on juvenile tissue, Greyed-Purple Group 184B. Underneath: Occasional prickle. Stipitate glands: Stipitate glands on margins.

*Petiole rachis.*—Length: 25 mm. Diameter: 2.0-2.5 mm. Color: Green Group 138A. Margins: Stipitate glands present. Prickles: Occasional. Stipitate glands: On margins.

*Leaflets.*—Size: Average size of the terminal leaflet is 60-65 mm (l)×55-60 mm (w). Shape: Ovate. Base: Broadly ovate. Apex: Acute Margins: Serrated. Texture: Thick and leathery.

Hips/seed formation: None observed.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant characterized by the following combination of characteristics:

(a) Forms attractive, long lasting cream white flowers;

(b) Exhibits uniform, upright and bushy growth habit;

(c) Propagates well using traditional methods, and;

(d) Exhibits very good resistance to disease under normal growing conditions, substantially as herein illustrated and described.

* * * * *

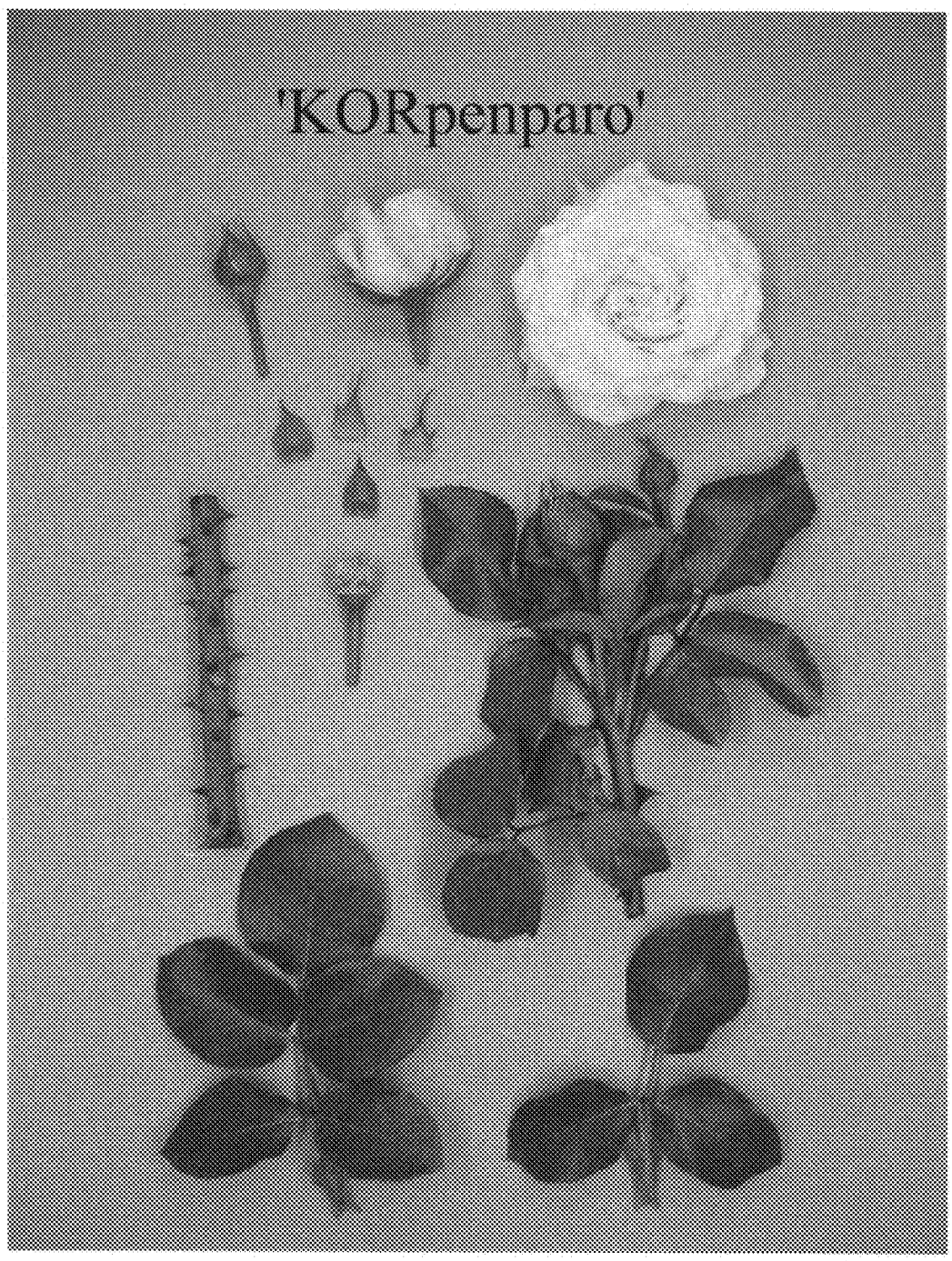
'KORpenparo'